United States Patent [19]

Butora et al.

[11] Patent Number: 5,424,456
[45] Date of Patent: Jun. 13, 1995

[54] N-ARYLALKYLDERIVATIVES OF 2-AMINOMETHYL-2,3-DIHYDRO-1,4-BENZODIOXINE AND THE PROCESS OF PREPARATION THEREOF

[75] Inventors: Gabriel Butora; Miroslav Rajsner; Ivan Helfert; Václav Trcka, all of Praha, Czechoslovakia

[73] Assignee: Vyzkumny Ustav Pro Farmacii A Biochemii s.p., Praha, Czechoslovakia

[21] Appl. No.: 150,047
[22] PCT Filed: May 27, 1992
[86] PCT No.: PCT/CS92/00015
§ 371 Date: Nov. 18, 1993
§ 102(e) Date: Nov. 18, 1993
[87] PCT Pub. No.: WO92/21671
PCT Pub. Date: Dec. 10, 1992

[30] Foreign Application Priority Data

May 31, 1991 [CS] Czechoslovakia ............. 1648-91

[51] Int. Cl.$^6$ ............................................. C07D 319/20
[52] U.S. Cl. ............................................. 549/366
[58] Field of Search ................................. 549/366

[56] References Cited

U.S. PATENT DOCUMENTS 3,444,210 5/1969 Moed et al. .
4,438,131 3/1984 Ehrmann et al. ............. 549/366

OTHER PUBLICATIONS

K. Mitani, et al., Novel Phenoxyalkylamine Derivatives. II. Synthesis and Calcium Ion Antagonistic Activities of Alpha–Alkyl–Alpha–[(phenoxypropylamino)Propyl]Benzeneacetonitrile Derivatives, *Chemical and Pharmaceutical Bulletin*, vol. 36, No. 1, Jan. 1988, pp. 373–385.

*Primary Examiner*—Nicky Chan
*Attorney, Agent, or Firm*—Cowan, Liebowitz & Latman

[57] ABSTRACT

New N-Arylalkylderivatives of 2-aminomethyl-2,3-dihydro-1,4-benzodioxine and its (+)- and (−)- enantiomers represented by general formula (I), where $R_1$, $R_2$ and $R_3$ represent H, or $R_1$ and $R_2$ represent H and $R_3$ represent H or $R_1$ and $R_2$ represent methoxy and $R_3$ represents H and their pharmaceutically acceptable organic or inorganic acid addition salts exhibit in pharmacological tests pronounced hypotensive activity as a result of their calcium channel blocking and alpha$_1$-adrenergic blocking activity and pronounced antithrombotic action. In a form of pharmaceutical preparations, they are suitable for the treatment and prevention of cardiovascular diseases and other disorders. New compounds of general formula (I) by N-alkylation of 2-aminomethyl-2,3-dihydro-1,4-benzodioxine and its (+)- and (−)-enantiomers by derivatives of 2 phenyl-2-isopropyl-5-oxovaleronitrile under the conditions of reductive alkylation or with derivatives of 5-bromo-2-phenyl-2-isopropylvaleronitrile, which can be prepared by allylation of alpha-isopropylbenzyl cyanide and subsequent addition of hydrogen bromide under free radical conditions to the obtained alpha-allyl-alpha-isopropylbenzyl cyanide and its derivatives.

1 Claim, No Drawings

N-ARYLALKYLDERIVATIVES OF 2-AMINOMETHYL-2,3-DIHYDRO-1,4-BENZODI-OXINE AND THE PROCESS OF PREPARATION THEREOF

This application is a 371 of PCT/CS92/00015 filed May 27, 1992.

TECHNICAL FIELD

The present invention relates to novel N-arylalkyl-derivatives of 2-aminomethyl-2,3-dihydro-1,4-benzodioxine and its enantiomers, the pharmaceutically acceptable acid addition salts thereof, and the process of preparation thereof. These compounds exhibit pronounced calcium channel blocking, $\alpha_1$-adrenergic as well as antithrombotic activities and can be used for treatment of hypertension and other cardiovascular diseases.

BACKGROUND ART

It is already known that the number of compounds represented by the general formula (II)

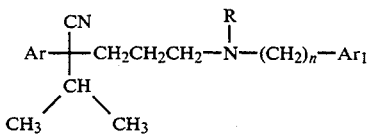

wherein Ar represents phenyl or substituted phenyl, R represents H or methyl, n is 2 or 3 and $Ar_1$ represents substituted phenyl, possess calcium channel blocking activity. From these substances Verapamil (generic name, Merck index, 11th Edition, 9851) represented by the general formula (II), wherein Ar and $Ar_1$ represent 3,4-dimethoxyphenyl, R represents methyl, n is 2, has effective calcium channel blocking activity and has been clinically used for the treatment of ischemic heart disease, arrhythmias and hypertension. In an advanced phase of clinical testing is Mepamil (proposed generic name) represented by the general formula (II), wherein Ar represents 2-methylphenyl, R represents methyl, n is 2 and $Ar_1$ represents 3,4-dimethoxyphenyl. The latter compound exhibits, compared to Verapamil, lower negative inotropic activity (Blaha L. et al. CS Patent 258534).

It is already known from the literature (Mitani K. et al.: Chem. Pharm. Bull., 36, 367 (1988), Mitani K. et al.: Chem. Pharm. Bull., 36, 373 (1988)), that compounds of general formula (II), wherein Ar represents phenyl, alkoxyphenyl, dialkoxyphenyl or trialkoxyphenyl group, R represents H or methyl, and $Ar_1$ represents substituted phenyloxy group exhibit calcium channel blocking and $\alpha$-adrenergic blocking activity.

Furthermore, it is known, that some derivatives of 2-aminomethyl-2,3-dihydro-1,4-benzodioxine, e.g. Piperoxan (generic name, Merck index, 11th Edition, 7448) block the $\alpha$-adrenergic receptors in a competitive manner and that the activity of the S-enantiomer is more pronounced, than that of the R-enantiomer (Nelson, L. N., Wennerstrom, J. E.: J. Med. Chem., 20, 880 (1977)).

According to our knowledge, derivatives of 2-aminomethyl-2,3-dihydro-1,4-benzodioxine exhibiting except of the $\alpha$-adrenergic blocking activity also calcium channel blocking activity have not been described yet.

DISCLOSURE OF INVENTION

As a result of extensive investigation, it has been found, that novel N-arylalkylderivatives of 2-aminomethyl-2,3-dihydro-1,4-benzodioxine and (+)-(−)-enantiomers thereof, represented by the general formula (I) wherein $R_1$ and $R_2$ represent methoxy and $R_3$ represents H (in further text assigned as VUFB 17951 for the hydrochloride of the racemic amine, VUFB 18019 for the hydrochloride of the (+)-enantiomer and VUFB 18020 for the hydrochloride of the (−)-enantiomer), or $R_1$ and $R_2$ represent H and $R_3$ represents methyl (in further text assigned as VUFB 17959 for the hydrochloride of the

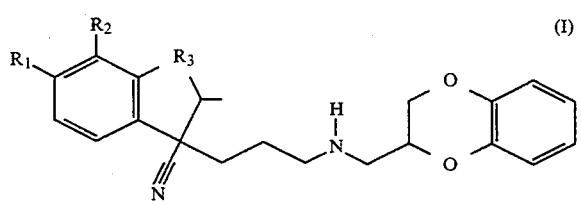

racemic amine, VUFB 18007 for the hydrochloride of the (+)-enantiomer and VUFB 18018 for the hydrochloride of the (−)-enantiomer) or $R_1$ and $R_2$ and $R_3$ represent H (in further text assigned as VUFB 18087 for the racemic amine) and the pharmaceutically acceptable acid addition salts thereof exhibit in pharmacological tests pronounced hypotensive activity as a result of a calcium channel blocking and $\alpha$-adrenergic blocking activity and a pronounced antithrombotic activity. In test animals they also lower intraocular pressure and lower the opening pressure of the urinary bladder sphincter.

Further, according to the present invention, processes are provided for preparation of the novel N-arylalkylderivatives of 2-aminomethyl- 2,3-dihydro-1,4-benzodioxine represented by the general formula (I), as well as pharmaceutical compositions; thereof and method of treating therewith.

According to the present invention, it has been found, that novel N-arylalkylderivatives of 2-aminomethyl-2,3-dihydro-1,4-benzodioxine and (+)- and (−)-enantiomers thereof represented by the general formula (I) wherein $R_1$ and $R_2$ represent methoxy and $R_3$ represents H (in further text assigned as VUFB 17951 for the hydrochloride of the racemic amine, VUFB 18019 for the hydrochloride of the (+)-enantiomer and VUFB 18020 for the hydrochloride of the (−)-enantiomer), or $R_1$ and $R_2$ represent H and $R_3$ represents methyl (in further text assigned as VUFB 17959 for the hydrochloride of the racemic amine, VUFB 18007 for the hydrochloride of the (+)-enantiomer and VUFB 18018 for the hydrochloride of the

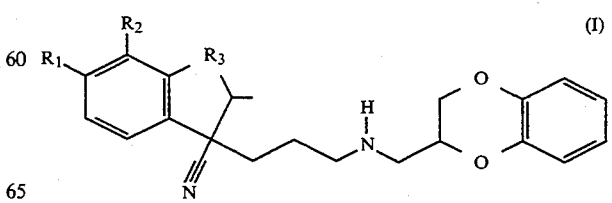

(−)-enantiomer) or $R_1$ and $R_2$ and $R_3$ represent H (in further text assigned as VUFB 18087 for the racemic amine) and the pharmaceutically acceptable acid addition salts thereof exhibit in pharmacological tests pronounced hypotensive activity as a result of a calcium channel blocking and α-adrenergic blocking activity and a pronounced antithrombotic activity. In test animals they also lower the intraocular pressure and the opening pressure of urinary bladder sphincter. These results are prerequisite for the use of these compounds for effective treatment of hypertension and other cardiovascular diseases, as well as dysuria and glaucoma in humans.

Compounds of the present invention represented by the general formula (I) and their pharmaceutically acceptable acid addition salts can be administered preferably in oral or parenteral form. For oral administration the active ingredient and the pharmaceutical carrier may, for example, take the form of pills, tablets (ev. with retarded release), granules, syrup or other liquid suspension or emulsion, whereas for parenteral administration the composition may be in the form of a sterile solution.

Pharmaceutically acceptable acid addition salts of the compounds represented by the formula (I) include for example mineral salts such hydrochloride, hydrobromide, hydroiodide, nitrate, sulfate, phosphate, and the like.; or organic acid salts such as acetate, maleate, fumarate, citrate, oxalate, malate, tartarate and the like.

The biological activity of the novel compounds represented by the general formula (I) can be illustrated by the results obtained in following tests:

1. CALCIUM CHANNEL BLOCKING ACTIVITY

The calcium channel blocking activity of the compounds was tested using a helically cut rat aortic strip in Krebs-Henselheit solution at 37° C., bubbled with a mixture of 95% $O_2$ and 5% $CO_2$. The isometrically registered contractions were induced by $K^{(+)}$ depolarization. The test compounds were applied in a cumulative doses and the vasodilating activity thereof was expressed in calculated concentration of the test compound, causing 50% decrease of contraction of the aortic strip ($IC_{50}$). The obtained results are shown in Table 1.

2. α-ADRENERGIC BLOCKING ACTIVITY a) The α-adrenergic blocking activity of the compounds was tested using a helically cut rat aortic strip in a Krebs-Henselheit solution at 37° C., bubbled with a mixture of 95% $O_2$ and 5% $CO_2$. Norepinephrine induced contractions were detected isometrically. The compounds were added in cumulative doses and the relaxing activity was expressed in per cents of the maximum norepinephrine contraction. The concentrations of the test compounds causing 50% relaxation are Shown in Table 2.

b) The α-adrenergic blocking activity of compounds VUFB 17951 and VUFB 17959 was also shown in the test of influencing the postdecapitation muscular contractions in rats. The test compounds were administered intravenously in the dose of 4.6 mg/kg for VUFB 17951 and 4.2 g/kg for VUFB 17959. Both compounds administered 30 minutes prior to decapitation caused a highly significant decrease in number of postdecapitation contractions.

3. HYPOTENSIVE ACTIVITY a) The blood pressure of pentobarbital anaesthesized rabbits was registered invasively in arteria femoralis. The average decrease in systolic (SBP) and diastolic (DBP) blood pressure expressed in per cents of the starting blood pressure level after intravenous and oral administration is shown in Tables 3 and 4.

b) The blood pressure of pentobarbital anaesthesized dogs was registered invasively in arteria femoralis. The average decrease in systolic (SBP) arid diastolic (DBP) blood pressure expressed in per cents of the starting blood pressure level after intravenous and oral administration is shown in Tables 5 and 6.

c) The blood pressure of conscious monkeys (*Macaca mulatta*) was measured non-invasively on the arm. The average decrease in systolic (SBP) and diastolic (DBP) blood pressure after intravenous and oral administration was expressed in per cents of the starting blood pressure. The results are shown in Tables 7 and 8.

4. ANTITHROMBOTIC ACTIVITY

The antithrombotic activity of the test compounds was established using the model of rat peripheral venous thrombosis in a closed abdominal part of vena cava. The thrombus was induced by intravenous administration of hypotonic solution of sodium chloride. The thrombus was freed 10 minutes after induction and weighted. The mass of thrombi in control animals was compared to the mass of thrombi of animals administered by the test compound. The statistically significant effective dose for compound VUFB 17951 was 0.5 mg/kg intravenously and 5 mg/kg orally and for the compound VUFB 17959 0.25 mg/kg and 1.0 mg/kg, respectively. The corresponding dose of a standard (Cilostazol, generic name, Merck index, 11th Edition, 2277) was 25 mg/kg orally.

5. EFFECT ON THE OPENING PRESSURE OF THE URINARY BLADDER SPHINCTER

Compounds VUFB 17951 and VUFB 17959 lowered the opening pressure of the urinary bladder sphincter of rats in corresponding doses in the same extent as prazosin (generic name, Merck index, 11th Edition, 7715) or terazosin (generic name, Merck index, 11th Edition, 9084), but with a longer duration of action.

6. EFFECT ON THE INTRAOCULAR PRESSURE

Compounds VUFB 17951 and VUFB 17959 lowered significantly the intraocular pressure of rabbits after topical intraocular administration.

Compounds, represented by the general formula (I) can be prepared, according to the present invention, by N-alkylation of the already known 2-aminomethyl-2,3-dihydro-1,4-benzodioxine (Augstein, J. et al. J. Med. Chem., 8, 446 (1965), DD Pat 55964; Chem. Abstr. 68, 59588 (1968)) and its optically active enantiomers (Stanlake, J. B. et all.: J. Phar. Bull., 20, 82 (1968) with known aldehydes of the general formula (III)

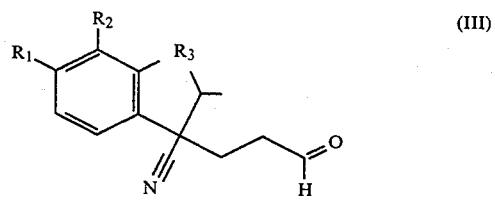

wherein $R_1$, $R_2$ and $R_3$ have the same meaning as in (I) (DE-OS 2631222; Chem. Abstr. 88, 169796 (1978), Blaha, L. et al. CS Patent 258534 (1986), Mitani, K. et al. Chem. Pharm. Bull., 36, 373 (1988)) under the conditions of reductive alkylation. As reducing agent for the reduction of the Schiff base formed in the reaction sodium borohydride in methanol or ethanol, catalytic hydrogenation in a solution of a lower aliphatic alcohol with 1 to 4 carbon atoms using PrO2 or Pd on a suitable carrier e.g. charcoal at the temperature ranging from 20° to 40 ° C., or formic acid in a suitable organic solvent e.g. toluene preferably at the boiling point of the reaction mixture until the evolution of carbon dioxide ceased, can be used. The product of the reaction represented by the general formula (I) can be isolated from the reaction mixture in the form of a base and can be transformed using organic or inorganic acids to a acid addition salt.

A further process for preparation of compounds represented by the general formula (I) is the alkylation of 2-aminomethyl-2,3-dihydro-1,4-benzodioxine and its enantiomers with the halogen-derivatives of a general formula (IV) wherein the substituents $R_1$, $R_2$ and $R_3$ have the same meaning as in

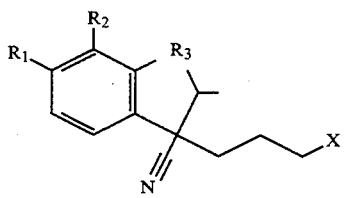
(IV)

(I) and X represents Cl or Br. The more reactive bromo derivatives can be, according to this invention, prepared by addition of hydrogen bromide under free radical conditions to α-allyl-α-isopropylbenzyl cyanide represented by the general formula (V) where the substituents $R_1$, $R_2$ and $R_3$ have the same meaning as in

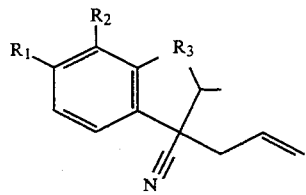
(V)

(I). The addition of hydrogen bromide can be performed by introduction of hydrogen bromide into a solution of the allyl derivative represented by the general formula (V) preferably in non-polar solvent e.g. cyclohexane or toluene in the presence of catalytic amount of radical producers e.g. dibenzoyl peroxide or azobisisobutyronitrile maintaining the reaction mixture at temperature ranging from 10° to 60 ° C. The alkylation of 2-aminomethyl-2,3-dihydro-1,4-benzodioxine and its enantiomers can be performed by heating the reaction components without, or in a suitable organic solvent e.g. toluene, ethanol, acetone, xylene or dimethylformamide at temperature ranging from 80° to 140° C. for 6 to 24 hours in the presence of organic or inorganic compounds capable of neutralizing the hydrogen bromide formed during the reaction. The basic product of the general formula (I) formed in the reaction can be isolated by diluting the reaction mixture with water and by extraction of the product into a suitable, in water immiscible organic solvent, e.g. toluene and by evaporating the solvent. The obtained crude base can be transformed into a acid addition salt by neutralization with a inorganic or organic acid.

The allyl derivatives represented by the general formula (V) can be, according to the present invention, prepared from the benzyl cyanide of the general formula (VI)

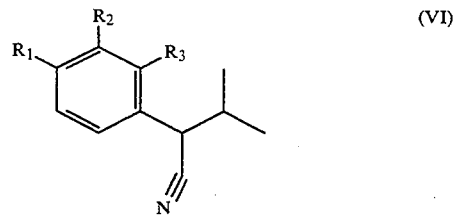
(VI)

where the substituents $R_1$, $R_2$ and $R_3$ have the same meaning as in (I) with allylchloride or allylbromide in a water solution of sodium hydroxide in the presence of a quaternary ammonium salt, e.g. tetrabutylammonium hydrogen sulfate at the temperature ranging from 20° to 60 ° C.

The present invention is further illustrated by the following examples but it is to be understood that present invention is not limited in terms of the specific process conditions.

MODES OF CARRYING OUT THE INVENTION

EXAMPLE 1

α-Allyl-α-isopropyl-2-methylbenzyl cyanide

To a solution of 362 g of sodium hydroxide in 362 ml of demineralized water 216.6 g of α-isopropyl-2-methylbenzyl cyanide and 6.4 g of tetrabutylammonium hydrogen sulfate were added, and the mixture was heated to 40° C. with intensive stirring. During 3hours 287 g of allylchloride was added. During, the addition and for further two hours the temperature of the reaction mixture was maintained at 40° C. and thereafter at 60° C. for additional three hours. After cooling to room temperature, the reaction mixture was diluted with 550 ml of water and the product was extracted into toluene. After washing with water until neutral pH and drying with anhydrous magnesium sulfate, the solvent was evaporated and the residue was distilled under diminished pressure to obtain 249 g (93%) of the desired compound, b.p. 122°-124 ° C./333 Pa.

Using the same procedure, the following compounds were obtained:

α-allyl-α-isopropyl-3,4-dimethoxybenzyl cyanide, (yield 97%, b.p. 120°-122° C./7 Pa, α-allyl-α-isopropylbenzyl cyanide, (yield 81%, b.p. 115°-117° C./330 Pa.

EXAMPLE 2

5-Bromo-2- isopropyl-2- (2-methylphenyl) valeronitrile

To a solution of 160 g of α-allyl-α-isopropyl -2-methyl- benzyl cyanide and 9 g of dry dibenzoyl peroxide in 750 ml of dry toluene gaseous hydrogen bromide was introduced with stirring for one hour. The temperature of the reaction mixture was kept, if necessary, by external cooling between 25° to 30 ° C. The reaction mixture was poured into 450 g of crushed ice. The separated toluene solution was washed with a solution of potassium carbonate until neutral pH and finally with water. The solvent was evaporated under diminished pressure to leave 216.3 g (99%) of the product, which can be used in further reaction steps without purification.

EXAMPLE 3

5-Bromo-2-(3,4-dimethoxyphenyl)-2- isopropyl valeronitrile

To a solution of 50 g of α-allyl-α-isopropyl-3,4-dimethoxy- benzyl cyanide and 2 g of azobisisobutyronitrile in 400 ml of cyclohexane (or n-hexane) gaseous hydrogen bromide was introduced for 70 minutes, when, according to GLC, the reaction mixture did not contain the starting allyl derivative. During the introduction of the hydrogen bromide, the reaction temperature raised to 40° C. The reaction mixture was neutralized with 200 ml of 30% solution of potassium carbonate. The separated cyclohexane solution of the product was washed with water until neutral pH. After drying and evaporating the solvent under diminished pressure, the crude product (61.7 g, 94%) was obtained, which could be used without purification in further reaction step.

Using the same procedure, 5-bromo-2-phenyl-2-isopropyl valeronitrile was obtained in 90% yield.

EXAMPLE 4

5-(2,3-Dihydro-1,4-benzodioxin-2-ylmethylamino)-2-(3,4-dimethoxyphenyl)-2-isopropyl valeronitrile Procedure A To a solution of sodium methoxide, obtained from 1.21 g of sodium and 50 ml of methanol, 10.7 g of 2-aminomethyl-2,3-dihydro-1,4-benzodioxine hydrochloride was added, followed by 24.0 g of 2-(3,4-dimethoxyphenyl)-2-isopropyl-5-oxovaleronitrile in 250 ml of methanol. The mixture was stirred at reflux temperature for 1 hour. After cooling to 5° C. 10.0 g of sodium borohydride was added in small portions and the reaction mixture was stirred without cooling for 2 hours, than left overnight at room temperature and finally refluxed for 1 hour. The solvent was distilled off and the residue was mixed with 550 ml of 3% hydrochloric acid. The non-basic products were removed by extraction into ether. The crude base was liberated by addition of sodium hydroxide and extracted into chloroform. After drying (with anhydrous sodium sulfate) and evaporating the solvent, 21.0 g (94%) of crude base was obtained, which was transformed into its hydrochloride via usual procedure. Melting point of the hydrochloride was 158°–165° C. after recrystallization from the mixture of acetone and diisopropyl ether.

Procedure B

The mixture of 19.8 g of 5-bromo-2-(3,4-dimethoxyphenyl)-2-isopropyl valeronitrile, 9.6 g of 2-aminomethyl-2,3-dihydro-1,4-benzodioxine in 20 ml of toluene and 6.2 g of potassium carbonate in 43 ml of water was refluxed with stirring for 24 hours. After cooling to room temperature, the reaction mixture was diluted with 150 ml of water and 150 ml of ether. After shaking the layers were separated. The water phase was extracted with ether. The combined organic layers were washed with water and dried with anhydrous sodium sulfate. The solvent was evaporated under diminished pressure to leave 24.5 g of oily crude base, which was transformed using etheral solution of hydrogen chloride into the hydrochloride (11.2 g, 42%), melting point 153°–160° C. (tetrahydrofuran-ether). Its C.H.N. analysis, 1H NMR and IR spectra were identical with those obtained via procedure A.

Using the same procedure, the following compounds were obtained:

5-[(+)-2,3-dihydro-1,4-benzodioxin-2-ylmethylamino]-2-(3,4-dimethoxyphenyl)-2-isopropyl valeronitrile by reductive alkylation of (+)-2-aminomethyl-2,3-dihydro-1,4-benzodioxine with 2-(3,4-dimethoxyphenyl)-2-isopropyl-5-oxo valeronitrile according to the procedure A, melting point of the hydrochloride 134°–139° C. (acetone-ether), $[\alpha]^{21}_D = 43.5°$ (C=0.405, methanol), 5-[(−)-2,3-dihydro-1,4-benzodioxin-2-ylmethylamino]-2-(3,4-dimeth-oxyphenyl)-2-isopropyl valeronitrile by reductive alkylation of (−)-2-aminomethyl-2,3-dihydro-1,4-benzodioxine with 2-(3,4-dimethoxyphenyl)-2-isopropyl-5-oxo valoronitrile according to the procedure A, melting point of the hydrochloride 129°–138° C. (acetone-ether), $[\alpha]^{21}_D = -43.92$ (c=0.405, methanol), 5-(2,3-dihydro-1,4-benzodioxin-2-ylmethylamino)-2-isopropyl-2-(2-methylphenyl) valeronitrile by reductive alkylation of 2-aminomethyl-2,3-dihydro-1,4-benzodioxine with 2-isopropyl-2-(2-methylphenyl)-5-oxo valeronitrile according to procedure A, yield 59%, melting point of the hydrochloride 120°–127° C. (acetone-ether). The hydrochloride crystallized from the mixture of methanol-diisopropylether formed a solvate with methanol, melting point 69°–78° C.; this compound was prepared according to the procedure B in 41% yield, 5-[(+)-2,3-dihydro-1,4-benzodioxin-2-ylmethylamino]-2-isopropyl-2- -(2-methylphenyl) valeronitrite by reductive alkylation of (+)-2-aminomethyl-2,3-dihydro-1,4-benzodioxine with 2-isopropyl-2-(2-methylphenyl)-5-oxo valeronitrile according to the procedure A, yield 68%, melting point of the hydrochloride, forming a solvate with methanol 62°–69 ° C. (methanol-ether), $[\alpha]^{21}_D = 44.37°$ (c=0.746, methanol), 5-[(−)-2,3-dihydro-1,4-benzodioxin-2-ylmethylamino]-2-isopropyl-2- -(2-methylphenyl) valeronitrile by reductive alkylation of (−)-2-aminomethyl-2,3-dihydro-1,4-benzodioxine according to the procedure A, yield 89%, melting point of the hydrochloride forming a solvate with methanol 54°–70° C. (methanol-ether), $[\alpha]^{21}_D = -45.47°$ (c=0.746, methanol), 5-(2,3-dihydro-1,4-benzodioxin-2-ylmethylamino)-2-phenyl-2-isopropyl valeronitrile by reductive alkylation of 2-aminomethyl-2,3-dihydro- -1,4-benzodioxine with 2-phenyl-2-isopropyl-5-oxo valeronitrile according to procedure A, yield 80%, melting point of the hydrochloride was 115°–123 ° C. (acetone-ether).

TABLE 1

| Calcium channel blocking activity | |
| --- | --- |
| Test compound | IC₅₀ (M) |
| VUFB 17951 | $1.8 \times 10^{-5}$ |
| VUFB 17959 | $1.6 \times 10^{-5}$ |
| VUFB 18007 | $1.5 \times 10^{-5}$ |
| VUFB 18018 | $1.5 \times 10^{-5}$ |
| VUFB 18019 | $1.6 \times 10^{-5}$ |
| VUFB 18020 | $2.5 \times 10^{-5}$ |
| VUFB 18087 | $8.5 \times 10^{-6}$ |

TABLE 2

| α-adrenergic blocking acitvity | |
| --- | --- |
| Test compound | IC₅₀ (M) |
| VUFB 17951 | $6 \times 10^{-6}$ |
| VUFB 17959 | $2.5 \times 10^{-5}$ |
| VUFB 18087 | $7.6 \times 10^{-5}$ |

TABLE 3

| | | Hypotensive activity (rabbits) | | | | | |
| --- | --- | --- | --- | --- | --- | --- | --- |
| test compound | i.v dose | blood pressure | \multicolumn{5}{c}{minutes after administration} | | | | |
| | | | 1 | 5 | 30 | 60 | 180 |
| VUFB 17951 | 0.2 mg/kg | SBP | −28 | −24 | −25 | −18 | −13 |
| | | DBP | −36 | −23 | −24 | −16 | −17 |

TABLE 3-continued

| test compound | i.v dose | blood pressure | \multicolumn{5}{c}{minutes after administration} |
|---|---|---|---|---|---|---|---|
| | | | 1 | 5 | 30 | 60 | 180 |
| | 1.0 mg/kg | SBP | −47 | −39 | −35 | −35 | −17 |
| | | DBP | −56 | −36 | −30 | −33 | −24 |
| VUFB 17959 | 1.0 mg/kg | SBP | −47 | −23 | −22 | −14 | −8 |
| | | DBP | −51 | −22 | −21 | −25 | −18 |
| | 5.0 mg/kg | SBP | −60 | −35 | −26 | −27 | −25 |
| | | DBP | −69 | −39 | −31 | −29 | −33 |
| VUFB 18087 | 4.0 mg/kg | SBP | −45 | −45 | −30 | −31 | −28 |
| | | DBP | −58 | −43 | −29 | −29 | −32 |
| | 0.4 mg/kg | SBP | −10 | −19 | −17 | −17 | −14 |
| | | DBP | −32 | −16 | −18 | −16 | −8 |

TABLE 4

Hypotensive activity (rabbits)

| test compound | p.o dose | blood pressure | \multicolumn{4}{c}{minutes after administration} |
|---|---|---|---|---|---|---|
| | | | 30 | 60 | 120 | 180 |
| VUFB 17951 | 5.0 mg/kg | SBP | −6 | −14 | −17 | −13 | −15 |
| | | DBP | −6 | −12 | −18 | −18 | −18 |
| | 10.0 mg/kg | SBP | −5 | −9 | −12 | −13 | −12 |
| | | DBP | −6 | −11 | −18 | −20 | −17 |
| VUFB 17959 | 10.0 mg/kg | SBP | −2 | −3 | −4 | −1 | +3 |
| | | DBP | −2 | 0 | −3 | −8 | −10 |
| | 50.0 mg/kg | SBP | −9 | −18 | −26 | −29 | −31 |
| | | DBP | −6 | −12 | −18 | −18 | −18 |

TABLE 5

Hypotensive activity (dogs)

| test compound | i.v dose | blood pressure | 5 | 30 | 60 | 180 |
|---|---|---|---|---|---|---|
| VUFB 17951 | 4.6 mg/kg | SBP | −46 | −48 | −42 | −40 | −31 |
| | | DBP | −53 | −49 | −47 | −42 | −34 |
| | 0.46 mg/kg | SBP | −46 | −47 | −41 | −41 | −26 |
| | | DBP | −52 | −46 | −40 | −36 | −28 |
| VUFB 17959 | 4.5 mg/kg | SBP | −43 | −43 | −31 | −23 | −17 |
| | | DBP | −63 | −46 | −29 | −25 | −14 |
| | 0.45 mg/kg | SBP | −16 | −23 | −14 | −13 | −6 |
| | | DBP | −52 | −23 | −16 | −16 | −2 |
| VUFB 18007 | 4.5 mg/kg | SBP | −47 | −33 | −27 | −22 | −17 |
| | | DBP | −66 | −41 | −25 | −19 | −12 |
| VUFB 18018 | 4.5 mg/kg | SBP | −40 | −42 | −30 | −22 | −21 |
| | | DBP | −54 | −46 | −29 | −24 | −22 |
| VUFB 18019 | 4.6 mg/kg | SBP | −17 | −32 | −26 | −16 | −14 |
| | | DBP | −54 | −32 | −8 | −14 | −8 |
| VUFB 18020 | 4.6 mg/kg | SBP | −46 | −58 | −43 | −35 | −40 |
| | | DBP | −63 | −63 | −45 | −37 | −34 |
| VUFB 18087 | 4.0 mg/kg | SBP | −49 | −32 | −31 | −27 | −22 |
| | | DBP | −62 | −31 | −31 | −26 | −26 |
| | 0.4 mg/kg | SBP | −33 | −29 | −29 | −19 | −4 |

TABLE 5-continued

Hypotensive activity (dogs)

| test compound | i.v dose | blood pressure | 5 | 30 | 60 | 180 |
|---|---|---|---|---|---|---|
| | | DBP | −37 | −27 | −27 | −13 | −13 |

TABLE 6

Hypotensive activity (dogs)

| test compound | p.o. dose | blood pressure | 15 | 30 | 60 | 120 | 300 |
|---|---|---|---|---|---|---|---|
| VUFB 17951 | 4.6 mg/kg | SBP | −9 | −11 | −14 | −19 | −24 |
| | | DBP | −9 | −11 | −13 | −14 | −19 |
| VUFB 17959 | 4.2 mg/kg | SBP | −5 | −16 | −18 | −20 | −23 |
| | | DBP | −5 | −20 | −20 | −20 | −21 |

TABLE 7

Hypotensive activity (monkeys)

| test compound | i.v. dose | blood pressure | 1 | 5 | 30 | 60 | 180 |
|---|---|---|---|---|---|---|---|
| VUFB 17951 | 1.0 mg/kg | SBP | −50 | −53 | −39 | −29 | −19 |
| | | DBP | −58 | −60 | −46 | −30 | −23 |
| | 0.25 mg/kg | SBP | −37 | −45 | −28 | −11 | −8 |
| | | DBP | −49 | −50 | −31 | −17 | −18 |
| VUFB 17959 | 1.0 mg/kg | SBP | −28 | −31 | −31 | −24 | −8 |
| | | DBP | −34 | −38 | −42 | −27 | −14 |
| | 0.25 mg/kg | SBP | −1 | −12 | −22 | −17 | −5 |
| | | DBP | −4 | −16 | −24 | −20 | −7 |

TABLE 8

Hypotensive activity (monkeys)

| test compound | p.o. dose | blood pressure | 0.5 | 1 | 3 | 5-6 | 24 |
|---|---|---|---|---|---|---|---|
| VUFB 17951 | 10.0 mg/kg | SBP | −26 | −24 | −21 | −23 | −9 |
| | | DBP | −30 | −27 | −26 | −29 | −11 |
| VUFB 17959 | 10.0 mg/kg | SBP | −20 | −15 | −17 | −11 | +1 |
| | | DBP | −16 | −15 | −16 | −10 | +5 |

We claim:

1. An arylalkyl derivative of 2-aminomethyl-2,3-dihydro-1,4-benzodioxine or its (+)- and (−)-enantiomers represented by the general formula (I)

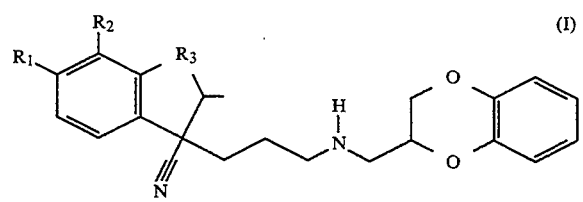

wherein $R_1$, $R_2$ and $R_3$ represent H, or $R_1$, $R_2$ represent $OCH_3$ and $R_3$ represents H, or $R_1$, $R_2$ represent H, and $R_3$ a represents $CH_3$, or the pharmaceutically acceptable acid addition salt thereof.

* * * * *

UNITED STATES PATENT AND TRADEMARK OFFICE
CERTIFICATE OF CORRECTION

PATENT NO. : 5,424,456
DATED : June 13, 1995
INVENTOR(S) : Gabriel Butora et al.

It is certified that error appears in the above-indentified patent and that said Letters Patent is hereby corrected as shown below:

On the title page: Items:

[75] Inventors: Gabriel Butora; Miroslav Rajsner; Ivan Helfert; Vaclav Trcka, all of Praha, Czech Republic

[73] Assignee: Vyzkummy Ustav Pro Farmacii A Biochemi˙ s.p., Praha Czech Republic Signed and Sealed this Ninth Day of April, 1996

Attest:

BRUCE LEHMAN

Attesting Officer          Commissioner of Patents and Trademarks